(12) United States Patent
Dipierro (10) Patent No.: US 9,555,227 B2
(45) Date of Patent: *Jan. 31, 2017

(54) BIOSYNCHRONOUS TRANSDERMAL DRUG DELIVERY

(71) Applicant: Chrono Therapeutics Inc., Hayward, CA (US)

(72) Inventor: Guy Dipierro, San Carlos, CA (US)

(73) Assignee: CHRONO THERAPEUTICS INC., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/746,704

(22) Filed: Jun. 22, 2015

(65) Prior Publication Data

US 2015/0283367 A1 Oct. 8, 2015

Related U.S. Application Data

(63) Continuation of application No. 14/162,156, filed on Jan. 23, 2014, now abandoned, which is a continuation
(Continued)

(51) Int. Cl.
*A61M 35/00* (2006.01)
*A61K 31/137* (2006.01)
*A61K 31/04* (2006.01)
*A61K 31/465* (2006.01)
*A61K 9/70* (2006.01)
(Continued)

(52) U.S. Cl.
CPC ............ *A61M 35/00* (2013.01); *A61K 9/0009* (2013.01); *A61K 9/703* (2013.01); *A61K 31/00* (2013.01); *A61K 31/04* (2013.01); *A61K 31/137* (2013.01); *A61K 31/465* (2013.01); *A61M 37/0015* (2013.01); *A61M 37/0092* (2013.01); *A61M 2037/0007* (2013.01); *A61M 2037/0023* (2013.01); *A61M 2037/0061* (2013.01); *A61N 1/30* (2013.01)

(58) Field of Classification Search
None
See application file for complete search history.

(56) References Cited

U.S. PATENT DOCUMENTS 4,379,454 A 4/1983 Campbell et al.
4,545,990 A 10/1985 Le Foyer de Costil et al.
(Continued)

FOREIGN PATENT DOCUMENTS

CA 2142871 A1 3/1994
DE 19958554 A1 1/2001
(Continued)

OTHER PUBLICATIONS

Huang et al.; Reissue U.S. Appl. No. 14/615,012 entitled "Portable Drug Delivery Device Including a Detachable and Replaceable Administration or Dosing Element," filed Feb. 2, 2015.
(Continued)

*Primary Examiner* — Isis Ghali
(74) *Attorney, Agent, or Firm* — Shay Glenn LLP (57) ABSTRACT

Systems and methods for synchronizing the administration of compounds with the human body's natural circadian rhythms and addiction rhythms to counteract symptoms when they are likely to be at their worst by using an automated and pre programmable transdermal or other drug administration system.

25 Claims, 5 Drawing Sheets

Related U.S. Application Data of application No. 11/162,517, filed on Sep. 13, 2005, now abandoned.

(60) Provisional application No. 60/609,418, filed on Sep. 13, 2004.

(51) Int. Cl.
  *A61K 9/00* (2006.01)
  *A61K 31/00* (2006.01)
  *A61M 37/00* (2006.01)
  *A61N 1/30* (2006.01)

(56) References Cited

U.S. PATENT DOCUMENTS

| | | |
|---|---|---|
| 4,708,716 A | 11/1987 | Sibalis |
| 4,772,263 A | 9/1988 | Dorman et al. |
| 4,853,854 A | 8/1989 | Behar et al. |
| 4,885,154 A | 12/1989 | Cormier et al. |
| 4,908,213 A | 3/1990 | Govil et al. |
| 4,917,676 A | 4/1990 | Heiber et al. |
| 4,917,895 A | 4/1990 | Lee et al. |
| 5,000,956 A | 3/1991 | Amkraut et al. |
| 5,013,293 A | 5/1991 | Sibalis |
| 5,049,387 A | 9/1991 | Amkraut |
| 5,097,834 A | 3/1992 | Skrabal |
| 5,120,545 A | 6/1992 | Ledger et al. |
| 5,130,139 A | 7/1992 | Cormier et al. |
| 5,149,719 A | 9/1992 | Ferber et al. |
| 5,221,254 A | 6/1993 | Phipps |
| 5,242,941 A | 9/1993 | Lewy et al. |
| 5,252,604 A | 10/1993 | Nagy et al. |
| 5,262,165 A | 11/1993 | Govil et al. |
| 5,273,755 A | 12/1993 | Venkatraman et al. |
| 5,273,756 A | 12/1993 | Fallon et al. |
| 5,304,739 A | 4/1994 | Klug et al. |
| 5,352,456 A | 10/1994 | Fallon et al. |
| 5,364,630 A | 11/1994 | Osborne et al. |
| 5,370,635 A | 12/1994 | Strausak et al. |
| 5,389,679 A | 2/1995 | Alliger |
| 5,393,526 A | 2/1995 | Castro |
| 5,405,614 A | 4/1995 | D'Angelo et al. |
| 5,415,629 A | 5/1995 | Henley |
| 5,445,609 A | 8/1995 | Lattin et al. |
| 5,451,407 A | 9/1995 | Cormier et al. |
| 5,464,387 A | 11/1995 | Haak et al. |
| 5,472,946 A | 12/1995 | Peck et al. |
| 5,501,697 A | 3/1996 | Fisher |
| 5,505,958 A | 4/1996 | Bello et al. |
| 5,516,793 A | 5/1996 | Duffy |
| 5,545,407 A | 8/1996 | Hall et al. |
| 5,596,994 A | 1/1997 | Bro |
| 5,601,839 A | 2/1997 | Quan et al. |
| 5,616,332 A | 4/1997 | Herstein |
| 5,618,557 A | 4/1997 | Wille et al. |
| 5,653,682 A | 8/1997 | Sibalis |
| 5,686,100 A | 11/1997 | Wille et al. |
| 5,688,232 A | 11/1997 | Flower |
| 5,697,896 A | 12/1997 | McNichols et al. |
| 5,716,987 A | 2/1998 | Wille |
| 5,722,418 A | 3/1998 | Bro |
| 5,733,259 A | 3/1998 | Valcke et al. |
| 5,785,688 A | 7/1998 | Joshi et al. |
| 5,797,867 A | 8/1998 | Guerrera et al. |
| 5,820,875 A | 10/1998 | Fallon et al. |
| 5,833,466 A | 11/1998 | Borg |
| 5,843,979 A | 12/1998 | Wille et al. |
| 5,865,786 A | 2/1999 | Sibalis et al. |
| 5,876,368 A | 3/1999 | Flower |
| 5,879,322 A | 3/1999 | Lattin et al. |
| 5,908,301 A | 6/1999 | Lutz |
| 5,919,156 A | 7/1999 | Stropkay et al. |
| 5,932,240 A | 8/1999 | D'Angelo et al. |
| 5,945,123 A | 8/1999 | Hermelin |
| 5,967,789 A | 10/1999 | Segel et al. |
| 5,993,435 A | 11/1999 | Haak et al. |
| 5,997,501 A | 12/1999 | Gross et al. |
| 6,018,679 A | 1/2000 | Dinh et al. |
| 6,019,997 A | 2/2000 | Scholz et al. |
| 6,059,736 A | 5/2000 | Tapper |
| 6,068,853 A | 5/2000 | Giannos et al. |
| 6,090,404 A | 7/2000 | Meconi et al. |
| 6,129,702 A | 10/2000 | Woias et al. |
| 6,165,155 A | 12/2000 | Jacobsen et al. |
| 6,211,296 B1 | 4/2001 | Frate et al. |
| 6,374,136 B1 | 4/2002 | Murdock |
| 6,423,747 B1 | 7/2002 | Lanzendörfer et al. |
| 6,436,078 B1 | 8/2002 | Svedman |
| 6,437,004 B1 | 8/2002 | Perricone |
| 6,539,250 B1 | 3/2003 | Bettinger |
| 6,567,785 B2 | 5/2003 | Clendenon |
| 6,576,269 B1 | 6/2003 | Korneyev |
| 6,579,865 B2 | 6/2003 | Mak et al. |
| 6,589,229 B1 | 7/2003 | Connelly et al. |
| 6,595,956 B1 | 7/2003 | Gross et al. |
| 6,638,528 B1 | 10/2003 | Kanios |
| 6,638,543 B2 | 10/2003 | Kang et al. |
| 6,723,086 B2 | 4/2004 | Bassuk et al. |
| 6,849,645 B2 | 2/2005 | Majeed et al. |
| 6,861,066 B2 | 3/2005 | Van de Casteele |
| 6,867,342 B2 | 3/2005 | Johnston et al. |
| 6,887,202 B2 | 5/2005 | Currie et al. |
| 7,019,622 B2 | 3/2006 | Orr et al. |
| 7,196,619 B2 | 3/2007 | Perlman et al. |
| 7,376,700 B1 | 5/2008 | Clark et al. |
| 7,780,981 B2 | 8/2010 | DiPierro et al. |
| 8,021,334 B2 | 9/2011 | Shekalim |
| 8,252,321 B2 | 8/2012 | DiPierro et al. |
| 8,372,040 B2 | 2/2013 | Huang et al. |
| 8,440,221 B2 | 5/2013 | Zumbrunn et al. |
| 8,574,188 B2 | 11/2013 | Potter et al. |
| 8,589,174 B2 | 11/2013 | Nelson et al. |
| 8,673,346 B2 | 3/2014 | Zumbrunn et al. |
| 8,690,827 B2 | 4/2014 | Edwards et al. |
| 8,727,745 B2 | 5/2014 | Rush et al. |
| 8,741,336 B2 | 6/2014 | DiPierro et al. |
| 8,865,207 B2 | 10/2014 | Kanios et al. |
| 8,999,356 B1 | 4/2015 | Ramirez et al. |
| 9,023,392 B2 | 5/2015 | Koo et al. |
| 9,155,712 B2 | 10/2015 | Kanios et al. |
| 9,238,108 B2 | 1/2016 | Edwards et al. |
| 2001/0022978 A1 | 9/2001 | Lacharriere et al. |
| 2002/0127256 A1 | 9/2002 | Murad |
| 2002/0165170 A1 | 11/2002 | Wilson et al. |
| 2002/0169439 A1 | 11/2002 | Flaherty |
| 2002/0182238 A1 | 12/2002 | Creton |
| 2003/0065294 A1 | 4/2003 | Pickup et al. |
| 2003/0065924 A1 | 4/2003 | Wuidart et al. |
| 2003/0083645 A1 | 5/2003 | Angel et al. |
| 2004/0019321 A1 | 1/2004 | Sage et al. |
| 2004/0062802 A1 | 4/2004 | Hermelin |
| 2004/0138074 A1 | 7/2004 | Ahmad et al. |
| 2004/0253249 A1 | 12/2004 | Rudnic et al. |
| 2004/0259816 A1 | 12/2004 | Pandol et al. |
| 2005/0002806 A1 | 1/2005 | Fuechslin et al. |
| 2005/0034842 A1 | 2/2005 | Huber et al. |
| 2005/0048020 A1 | 3/2005 | Wille |
| 2005/0141346 A1 | 6/2005 | Rawls et al. |
| 2005/0151110 A1 | 7/2005 | Minor et al. |
| 2006/0024358 A1 | 2/2006 | Santini et al. |
| 2006/0122577 A1 | 6/2006 | Poulsen et al. |
| 2006/0184093 A1 | 8/2006 | Phipps et al. |
| 2006/0188859 A1 | 8/2006 | Yakobi |
| 2006/0206054 A1 | 9/2006 | Shekalim |
| 2007/0042026 A1 | 2/2007 | Wille |
| 2007/0168501 A1 | 7/2007 | Cobb et al. |
| 2007/0191815 A1 | 8/2007 | DiPierro |
| 2007/0250018 A1 | 10/2007 | Adachi et al. |
| 2008/0201174 A1 | 8/2008 | Ramasubramanian et al. |
| 2009/0118710 A1 | 5/2009 | Kortzeborn |
| 2010/0114008 A1 | 5/2010 | Marchitto et al. |
| 2010/0280432 A1 | 11/2010 | DiPierro et al. |
| 2014/0200525 A1 | 7/2014 | DiPierro |

(56) References Cited

U.S. PATENT DOCUMENTS

| | | |
|---|---|---|
| 2014/0207047 A1 | 7/2014 | DiPierro et al. |
| 2014/0207048 A1 | 7/2014 | DiPierro et al. |
| 2014/0323423 A1 | 10/2014 | DiPierro et al. |

FOREIGN PATENT DOCUMENTS

| | | |
|---|---|---|
| DE | 10105759 C1 | 10/2001 |
| DE | 10103158 A1 | 8/2002 |
| EP | 0314528 B1 | 12/1992 |
| EP | 0354554 B1 | 1/1994 |
| EP | 726005 A1 | 8/1996 |
| EP | 0612525 B1 | 9/2001 |
| EP | 1662989 B1 | 9/2014 |
| JP | 2-202813 A | 8/1990 |
| JP | 9-512006 A | 12/1997 |
| JP | 2005525147 | 8/2005 |
| WO | WO86/07269 A1 | 12/1986 |
| WO | WO91/14441 A1 | 10/1991 |
| WO | WO95/06497 A1 | 3/1995 |
| WO | WO97/11741 A1 | 4/1997 |
| WO | WO97/18782 A1 | 5/1997 |
| WO | WO98/46093 A1 | 10/1998 |
| WO | WO00/74763 A2 | 12/2000 |
| WO | WO03/022349 A2 | 3/2003 |
| WO | WO2004/073429 A1 | 9/2004 |
| WO | WO2005/079161 A2 | 9/2005 |

OTHER PUBLICATIONS

Zumbrunn et al.; U.S. Appl. No. 14/746,689 entitled "Transdermal drug delivery method and system," filed Jun. 22, 2015.

Bruguerolle; Chronopharmacokinetics; Clin Pharmacokinet; 35(2); pp. 83-94; Aug. 1998.

Dockser-Marcus, A.; New research shows drugs work best at certain times; The Wall Street Journal; 6 pgs.; May 27, 2003; (http://www.wsj.com/articles/SB105397312486508700).

Ethicon Endo-Surgery, Inc.; Sedasys® Computer-assisted personalized sedation system essential product information; retrieved May 12, 2015 from the internet (http://www.sedasys.com/explore-the-system/essential-product-information); 2 pgs.

Gennaro (Editor); Remington: The Science and Practice of Pharmacy; 19th Ed.; Mack Publishing Co.; Easton, PA; p. 1582-1584; Jun. 1995.

Gries et al.; Importance of Chronopharmacokinetics in Design and Evaluation of Transdermal Drug Delivery Systems; J Pharmoacol Exp Ther; 285(2); pp. 457-463; May 1998.

Guy; Current status and future prospects of transdermal drug delivery; Pharm Res; 13(12); pp. 1765-1769; Dec. 1996.

Halberg et al.; Chronomics: circadian and circaseptan timing of radiotherapy, drugs, calories, perhaps nutriceuticals and beyond; Journal of Experimental Therapeutics and Oncology; 3(5); pp. 223-260; Sep. 2003.

Hrushesky; Temporally optimizable delivery systems: sine qua non for the next therapeutic revolution; J Cont Rel; 19(1-3); pp. 363-368; Mar. 1992.

Huang et al.; Inhibitory effects of curcumin on in vitro lipoxygenase and cyclooxygenase activities in mouse epidermis; Cancer Res; 51(3); pp. 813-819; Feb. 1991.

Kalish et al.; Prevention of contact hypersensitivity to topically applied drugs by ethacrynic acid: potential application to transdermal drug delivery; J. Controll Rel; 48(1); pp. 79-87; Sep. 1997.

Kalish et al.; Sensitization of mice to topically applied drugs: albuterol, chlorpheniramine, clonidine and nadolol; Contact Dermatitis; 35(2); pp. 76-82; Aug. 1996.

Kydonieus et al. (Editors); Biochemical Modulation of Skin Reactions; CRC Press; Boca Ratan, FL; pp. 9-10; Dec. 1999.

Labrecque, G. et al.; Chronopharmacokinetics; Pharmaceutical News; 4(2); pp. 17-21; 1997 (year of pub. sufficiently earlier than effective US filing date and any foreign priority date).

Lamberg; Chronotherapeutics: Implications for drug therapy; American Pharmacy; NS31(11); pp. 20-23; Nov. 1991.

Laser et al.; A review of micropumps; J. of Micromech. and Microeng.; 14; pp. R35-R64; Apr. 2004.

Lemmer; Clinical Chronopharmacology: The Importance of Time in Drug Treatment, in Ciba Foundation Symposium 183—Circadian Clocks and their Adjustment (eds. Chadwick and Ackrill); John Wiley & Sons, Inc.; pp. 235-253; Apr. 1995.

Lemmer; Implications of chronopharmacokinetics for drug delivery: antiasthmatics, H2-blockers and cardiovascular active drugs; Adv Drug Del Rev; 6(1); pp. 83-100; Jan./Feb. 1991.

Lemmer; The clinical relevance of chronopharmacology in therapeutics; Pharmacological Research; 33(2); pp. 107-115; Feb. 1996.

LeWitt et al.; New developments in levodopa therapy; Neurology; 62(No. 1, Suppl. 1); pp. S9-S16; Jan. 2004.

Maillefer et al.; A high-performance silicon micropump for an implantable drug delivery system; 12th IEEE Int'l Conf. on Micro Electro Mechanical Systems; MEMS '99; Orlando, FL; pp. 541-546; Jan. 1999.

Medtronic; MiniMed Paradigm® Veo(TM) System (product info.); retrieved May 12, 2015 from the internet: (http://www.medtronic.co.uk/your-health/diabetes/device/insulin-pumps/paradigm-veo-pump/); 3 pgs.

Molander et al.; Reduction of tobacco withdrawal symptoms with a sublingual nicotine tablet: A placebo controlled study; Nictonie & Tob. Res.; 2(2); pp. 187-191; May 2000.

Murphy et al.; Transdermal drug delivery systems and skin sensitivity reactions. Incidence and management; Am. J. Clin Dermatol.; 1(6); pp. 361-368; Nov./Dec. 2000.

Mutalik et al.; Glibenclamide transdermal patches: physicochemical, pharmacodynamic, and pharmacokinetic evaluation; J Pharm Sci; 93(6); pp. 1577-1594; Jun. 2004.

Nakadate et al.; Effects of chalcone derivatives on lipoxygenase and cyclooxygenase activities of mouse epidermis; Prostaglandins; 30(3); pp. 357-368; Sep. 1985.

Newmark; Plant phenolics as potential cancer prevention agents; Chapter 3 in Dietary Phytochemicals in Cancer Prevention; Chap. 3; Adv. Exp. Med. Biol. 401; pp. 25-34; 1996 (year of pub. sufficiently earlier than effective US filing date and any foreign priority date).

Ohdo; Changes in toxicity and effectiveness with timing of drug administration: implications for drug safety; Drug Safety; 26(14); pp. 999-1010; Dec. 2003.

Olsson et al.; A valve-less planar pump in silicon; IEEE; The 8th International Conference on Solid-State Sensors and Actuators; vol. 2; pp. 291-294, Jun. 1995.

Olsson et al.; An improved valve-less pump fabricated using deep reactive ion etching; Proc. of the IEEE, 9th Int'l Workshop on MEMS; San Diego, CA; pp. 479-484; Feb. 11-15, 1996.

Priano et al.; Nocturnal anomalous movement reduction and sleep microstructure analysis in parkinsonian patients during 1-night transdermal apomorphine treatment; Neurol Sci.; 24(3); pp. 207-208; Oct. 2003.

Prosise et al.; Effect of abstinence from smoking on sleep and daytime sleepiness; Chest; 105(4); pp. 1136-1141; Apr. 1994.

Redfern et al.; Circadian rhythms, jet lag, and chronobiotics: An overview; Chronobiology International; 11(4); pp. 253-265; Aug. 1994.

Reinberg; Concepts of Circadian Chronopharmacology; Annals of the New York Academy of Sciences; 618 (Temporal Control of Drug Delivery); pp. 102-115; Feb. 1991.

Shin et al.; Enhanced bioavailability of triprolidine from the transdermal TPX matrix system in rabbits; Int. J. Pharm.; 234(1-2); pp. 67-73; Mar. 2002.

Singer et al.; Nightmares in patients with Alzheimer's disease caused by donepezil: Therapeutic effect depends on the time of intake; Nervenarzt; 76(9); pp. 1127-1129; Sep. 2005 (Article in German w/ Eng. Summary).

Star Micronics Co., Ltd; Prototype Diaphragm Micro Pump SDMP305 (specifications); retrieved May 12, 2015 from the internet archive as of Jul. 2006 (http://www.star-m.jp/eng/products/develop/de07.htm); 3 pgs.

(56) References Cited

OTHER PUBLICATIONS

Thiele et al. (Ed.); Oxidants and Antioxidants in Cutaneous Biology: Current Problems in Dermatology (Book 29); S. Karger; 196 pgs.; Feb. 2001.
Wille et al.; cis-urocanic Acid Induces Mast Cell Degranulation and Release of Preformed TNF-alpha: A Possible Mechanism Linking UVB and cis-urocanic Acid to Immunosuppression of Contact Hypersensitivity; Skin Pharm Appl Skin Physiol; 12(1-2); pp. 18-27; Jan. 1999.
Wille et al.; Inhibition of irritation and contact hypersensitivity by ethacrynic acid; Skin Pharm Appl Skin Physiol; 11(4-5); pp. 279-288; Jul. 1998.
Wille et al.; Inhibition of Irritation and Contact Hypersensitivity by Phenoxyacetic Acid Methyl Ester in Mice; Skin Pharm Appl Skin Physiol; 13(2); pp. 65-74; Mar. 2000.
Wille et al.; Several different ion channel modulators abrogate contact hypersensitivity in mice; Skin Pharm Appl Skin Physiol; 12(1-2); pp. 12-17; Jan. 1999.
Wille, J.; Novel topical delivery system for plant derived hydrophobic anti-irritant active (presentation abstract No. 273); 226th ACS National Meeting; New York, NY; Sep. 7-11, 2003.
Wille; In Closing: an editorial on Plant-Derived Anti-irritants. Cosmetics & Toiletries, 118 (8), Aug. 2003.
Wille; Novel plant-derived anti-irritants; (presented Dec. 5-6, 2002 at the 2002 Ann. Scientific Mtg. & Tech. Showcase); J. Cosmet. Sci.; 54; pp. 106-107; Jan./Feb. 2003.
Wille; Thixogel: Novel topical delivery system for hydrophobic plant actives; in ROSEN (Ed.) Delivery System Handbook for Personal Care and Cosmetic Products; 1st Ed.; ISBN: 978-0-8155-1504-3; pp. 762-794; Sep. 2005.
Youan; Chronopharmaceutics: gimmick or clinically relevant approach to drug delivery?; J Cont Rel; 98(3); pp. 337-353; Aug. 2004.
Yun et al.; A distributed memory MIMD multi-computer with reconfigurable custom computing capabilities; IEEE; Proc. Int'l Conf. on Parallel and Distributed Systems; pp. 8-13; Dec. 10-13, 1997.
Netzel et al.; U.S. Appl. No. 15/009,683 entitled "Drug delivery methods and systems," filed Jan. 28, 2016.

BIOSYNCHRONOUS TRANSDERMAL DRUG DELIVERY

CROSS REFERENCE TO RELATED APPLICATIONS

This application is a continuation of U.S. patent application Ser. No. 14/162,156 filed on Jan. 23, 2014, which is a continuation of U.S. patent application Ser. No. 11/162,517 filed on Sep. 13, 2005, now abandoned, which claims the benefit of U.S. Provisional Application No. 60/609,418 filed on Sep. 13, 2004 which are incorporated herein by reference.

This application also relates to PCT application No. PCT/IB2004/002947 entitled Transdermal Drug Delivery Method and System filed on Sep. 13, 2004 which is incorporated herein by reference.

FIELD OF THE INVENTION

The present invention relates, in general, to controlled drug delivery methods and systems, and, more specifically, to systems and methods for bisynchronous transdermal drug delivery in which drugs, pharmaceuticals, and other bioactive substances are delivered transdermally into a body in a manner that is synchronized with biological processes and/ or biological rhythms so as to improve performance of the substance in the body.

RELEVANT BACKGROUND

In the field of drug delivery, it is recognized that supplying the drug in a correct temporal pattern is an important attribute of any drug delivery methodology. Controlled release drug delivery systems are intended to improve response to a drug and/or lessen side effects of a drug. The term "controlled release" refers generally to delivery mechanisms that make an active ingredient available to the biological system of a host in a manner that supplies the drug according to a desired temporal pattern. Controlled release drug delivery may be implemented using instantaneous release systems, delayed release systems, and sustained release systems. In most cases, controlled release systems are designed to maintain a sustained plasma level of an active ingredient in a drug within a human or animal host over a period of time.

Instantaneous release refers to systems that make the active ingredient available immediately after administration to the biosystem of the host. Instantaneous release systems include continuous or pulsed intravenous infusion or injections. Such systems provide a great deal of control because administration can be both instantaneously started and stopped and the delivery rate can be controlled with great precision. However, the administration is undesirably invasive as they involve administration via a puncture needle or catheter. 'Delayed release' refers to systems in which the active ingredient made available to the host at some time after administration. Such systems include oral as well as injectable drugs in which the active ingredient is coated or encapsulated with a substance that dissolves at a known rate so as to release the active ingredient after the delay. Unfortunately, it is often difficult to control the degradation of the coating or encapsulant after administration and the actual performance will vary from patient to patient. Sustained Release generally refers to release of active ingredient such that the level of active ingredient available to the host is maintained at some level over a period of time. Like delayed release systems, sustained release systems are difficult to control and exhibit variability from patient to patient. Due to the adsorption through the gastrointestinal tract, drug concentrations rise quickly in the body when taking a pill, but the decrease is dependent on excretion and metabolism, which cannot be controlled. In addition, the adsorption through the gastrointestinal tract in many cases leads to considerable side effects (such as ulcers), and can severely damage the liver.

Transdermal drug delivery has developed primarily for sustained release of drugs in situations where oral sustained release systems are inadequate. In some cases, drugs cannot be effectively administered orally because the active ingredients are destroyed or altered by the gastrointestinal system. In other cases the drug may be physically or chemically incompatible with the coatings and/or chelating agents used to implement sustained release. In other cases a transdermal delivery system may provide sustained release over a period of days or weeks whereas orally administered drugs may offer sustained performance over only a few hours. A wide variety of active substances can be delivered through transdermal systems so long as the active substance can be provided in a form that can cross the skin barrier.

In most cases transdermal delivery systems are passive, taking the form of a patch that is adhesively attached to the host. The patch includes a quantity of the active substance, along with a suitable carrier if need be, absorbed in a sponge or similar system. Once applied, the active ingredient diffuses into the host through the skin at a rate determined by the concentration of the active substance and the diffusivity of the active substance. However, a variety of physical and chemical processes at the skin/patch boundary affect the delivery rate and may eventually inhibit drug delivery altogether. Active transdermal delivery systems have been developed to help regulate the delivery rate by providing mechanisms to improve drug delivery over time by "pumping" the active ingredient. One such system is described in U.S. Pat. No. 5,370,635 entitled "DEVICE FOR DELIVERING A MEDICAMENT" which describes a system for delivering a medicament and dispensing it to an organism for a relatively long period of time, for example at least a few days. The device can be adapted for positioning on the surface of the skin of a human or possibly an animal body in order to apply a medicament thereto from the outer side thereof.

Conventional transdermal systems circumvent the disadvantages of the adsorption through the gastrointestinal tract, but they do not optimize or tailor the dosing regiment to offset peak symptoms. In addition the constant transdermal delivery of a drug can lead to severe side effects, including debilitating sleep disorders and ever increasing tolerance.

Timed delivery is most often used to maintain a sustained level of a drug in the body. A significant focus of current research in drug delivery has been to determine the influence of a patient's circadian or other biological rhythms on drug efficacy and efficiency. This research demonstrates that certain disease symptoms follow a daily pattern, with peak symptoms at certain times of the day. It has been widely acknowledged that hormones, neurotransmitters and other intra-body compounds are released in different amounts at different times of the day pursuant to daily patterns. The Wall Street Journal reported on May 27, 2003 that "Doctors are increasingly looking at the clock when it comes to prescribing medicine, instructing patients not only to what drug to use but also precisely when to take it. The new approach stems from a growing body of research that demonstrates that certain diseases tend to get worse at certain times of the day, By synchronizing medications with a patient's body clock, many physicians believe that the drugs will work more effectively and with fewer side effects. In some cases, the improvements have been so pronounced that doctors have been able to reduce dosages." Similarly, American Pharmacy reports that "Circadian physiologic processes alter drug absorption, distribution, metabolism, and excretion. As a result, drug doses need to be adjusted to meet the differing needs of target organs or tissues at various times of the day." See, L. Lamberg, American Pharmacy, 1991; N831(11): 20-23. Doctors have responded to this growing body of research by prescribing a carefully timed drug administration regimen to optimize treatment.

Recently, an orally administered drug for arthritis treatment has suggested a chronotherepeutic approach using a delay release system where the delay is scheduled to release the active ingredient at the beginning of an interleukin 6 cascade that is believed to cause early morning stiffness in rheumatoid arthritis patients. By attempting to synchronize the drug delivery with a biological cycle it is believed that low doses may be used to achieve desired results. However, this system does not overcome the limitations of delayed release systems described above. Although it is possible to meet the requirements of chronopharmacology with pills, this requires an enormous amount of discipline by the patient to comply with the treatment regiment. As illustrated above, to achieve optimal results, many patients may need to wake up during the night to take their medication.

Hence, what is needed is a reliable means of delivering multiple drugs in precisely timed and measured doses—without the inconvenience and hazard of injection, yet with improved performance as compared to orally-delivered drugs.

Currently, patient compliance (taking the proper dosages at the prescribed times) is a critical problem facing caregivers and pharmaceutical firms alike. Studies show that only about half of patients take medications at the times and in the dosages directed by their physician. It is reported that each year, 125,000 deaths and up to 20% of all hospital and nursing home admissions result from patient non-compliance. It is estimated that non-compliance results in additional healthcare costs in excess of $100 billion per year in United States. These figures are even more pronounced for the elderly. Hence, a need exists for systems and methods that increase patient compliance for administration of a variety of drugs.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

SUMMARY OF THE INVENTION

Briefly stated, the present invention involves synchronizing the administration of compounds with the human body's natural circadian rhythms and addiction rhythms to counteract symptoms when they are likely to be at their worst by using an automated and pre programmable transdermal or other drug administration system.

Specifically, this invention describes a method to maximize the efficiency of compound administration, decrease negative side effects and increase the efficacy of pharmacological therapy by synchronizing and tailoring the administration of certain compounds to match these circadian rhythms.

Thus based on an analysis of the human body's circadian rhythms, the invention delivers varying dosages at varying times, pursuant to a pre-programmed dosage profile. This ensures that peak drug concentrations are present in the bloodstream to offset peak disease and addiction symptoms arising from variances and fluctuation in the body's natural circadian rhythms. Further, these methods ensure that less of a drug is in the bloodstream when disease and addiction symptoms are at their lowest.

The present invention describes methods for treating diseases, addictions and disorders in humans. These methods involve synchronizing and tailoring the administration of compounds with the body's natural circadian rhythms to counteract symptoms when they are likely to be at their worst by using an automated and pre programmable transdermal drug administration system.

More specifically, these methods synchronize and tailor drug administration to the human body's circadian rhythms to deliver varying dosages at varying times. This ensures that peak drug concentrations are present in the bloodstream to offset peak disease and addiction symptoms arising from variances and fluctuation in the body's natural circadian rhythms. Further, these methods ensure that less of a drug is in the bloodstream when disease and addiction symptoms are at their lowest. This minimizes negative side effects, and increases efficacy of the dosing regimen.

DETAILED DESCRIPTION OF THE PREFERRED EMBODIMENTS

The reality of circadian rhythms in animals including humans is well known. Biological rhythms are periodic fluctuations in biological characteristics over time, which also include circadian as well as seasonal variations. Circadian, or approximately 24-hour, rhythms include the production of biological molecules such as cortisol and adrenaline, the regulation of body temperature and heart rate, changes in characteristics of blood, such as stickiness, and behaviors such as wakefulness, sleep and periods of activity.

Research demonstrates that certain disease symptoms follow a daily pattern, with peak symptoms at certain times of the day. It has been widely acknowledged that hormones, neurotransmitters and other intra-body compounds are released in different amounts at different times of the day pursuant to daily patterns. It is believed that the failure of current transdermal systems to synchronize drug administration with the body's natural rhythms often lead to (i) severe side effects, including debilitating sleep disorders (in the context of nighttime nicotine administration, for example), (ii) ever increasing tolerance (in the case of nitroglycerin and other pharmaceuticals for example), (iii) more expensive therapies, since more of a compound is needed since body rhythm tailored dosing is not implemented. In addition, many addictions follow a daily pattern consistent with one's circadian rhythms. For example, according to studies performed, immediately upon waking, smoker's have peak nicotine cravings. These peak cravings return after each meal, due to the interplay of serotonin release as a trained response to the culmination of a meal. Our methods precisely time the administration of drugs so that they reach peak levels when symptoms are likely to be at their worst, and efficacy is greatly improved.

The present invention involves precisely timing the administration of drugs so that they reach peak levels in synchronization with times when symptoms are likely to be at their worst, or times at which the drugs are believed to be more effective in the body and/or better tolerated by the patient. The present invention is described in terms of a particular example drug delivery system that provides automated and precise control over dosing, with single-dose capability, (once while people sleep) or capability to administer separate and varying-sized doses many times throughout a multiple day period. The particular implementation is consistent with a commercial development of a miniaturized, automated and programmable non-invasive drug delivery system called the ChronoDose™ system being developed by the assignee of the present invention. The system enables controlling of the amount of drug exposed to the skin in a controlled time dependent way according to a programmed administration schedule that implements a desired dosage profile. In this manner the present invention enables one to precisely control and vary the time of drug release and the amount of each dose, pursuant to an easily set pre-programmed dosage profile.

Research demonstrates that for certain symptoms, conditions and diseases, drug effects can be optimized when administered in a defined (and often varying) dosage at predefined times. This is known as Chrono-Pharmacology. To illustrate the importance of Chrono-Pharmacology consider the following facts:

Asthma attacks are 100 times more likely between 4:00 and 6:00 AM.

Heart attacks and strokes are most likely to occur around 6:00 AM.

Variant Angina attacks occur 30 times more often in the middle of the night between 2:00 AM and 4:00 AM.

Smokers experience the highest cravings immediately upon waking up.

Lethargy and difficulty getting out of bed is highest immediately upon waking up early in the morning.

Cold and flu symptoms peak during night time and early morning hours, when cold medications are wearing off.

Figure 1:
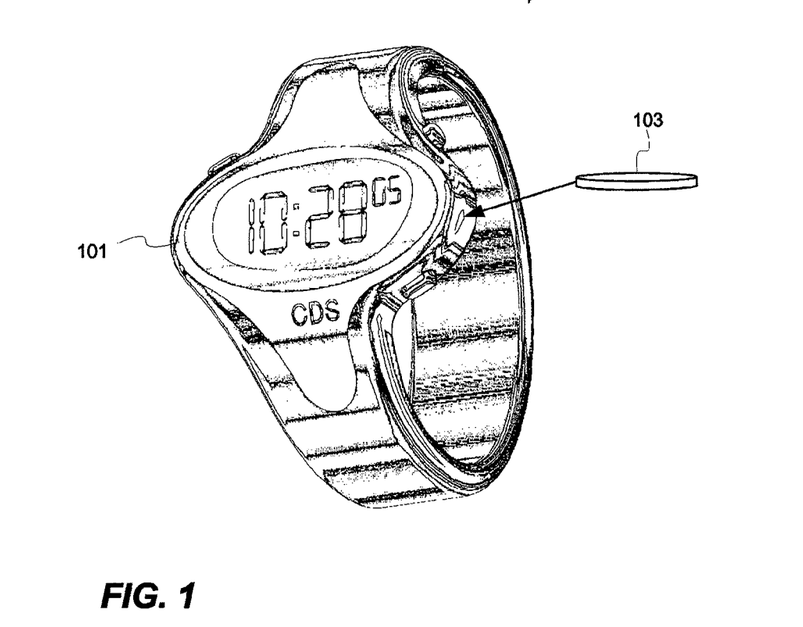
FIG. 1 shows an exemplary device useful for implementing the present invention.

In accordance with the present invention, substances with proven or suspected chrono-pharmacological efficiency are integrated into a miniaturized, automated, programmable watch-like device, such as device 100 shown in FIG. 1. The delivery system 100 shown in FIG. 1 can be used for a variety of active compositions, and is small, fully automated and programmable. This system consists of a re-usable wristwatch-like device 101 to control the time and dosage of drug delivery; and a small, disposable, 'reservoir' 103, which is about the size of a quarter or ½ dollar coin in a particular example, that the user can simply pop-in to place on the watch-like platform. This reservoir patch lasts, for example, up to 72 hours, depending on the application. Shorter and longer reservoir lifetimes are contemplated. The device is readily adapted to be worn on the forearm, ankle, or other convenient body location.

In a particular application the replaceable reservoir can include a description of an administration schedule that can be used to manually or automatically program device 100 with an administration schedule. For example, written schedule can be printed on or affixed to the reservoir 101 or electrically programmed using volatile or non-volatile memory. In this manner a dosing profile can be prescribed and filled by a pharmacy in much the same manner as a conventional drug prescription is handled today.

Figure 3:
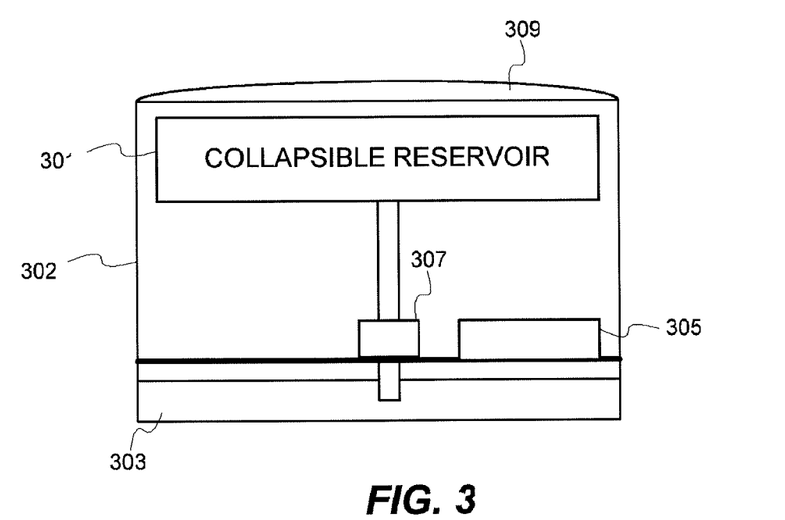
FIG. 3 is a schematic illustration of a drug delivery device in accordance with the present invention.

An exemplary implementation shown in FIG. 3 comprises a collapsible drug reservoir, an expandable waste reservoir, a micro-pump, electronics for automation, a display, and a highly permeable membrane. An exemplary system is described in a PCT application No. PCT/IB2004/002947 entitled TRANSDERMAL DRUG DELIVERY METHOD AND SYSTEM filed on Sep. 13, 2004 which is incorporated herein by reference. The drug reservoir will contain about 3 ml of drug formulation. A tiny, miniaturized pump is activated at pre-programmed times and releases a pre-defined amount of drug formulation into the drug chamber, where the formulation comes into contact with highly permeable membrane. This membrane rests on the skin, and provides for even diffusion of the drug over the device's drug absorption surface area. This membrane works effectively with, and can be coated with, an adhesive. In operation, when the administration of the drug needs to be discontinued, the remaining drug formulation is either removed from the membrane area via a waste chamber, containing a hydrophilic substance (hydrogel) or the device is taken off.

Figure 4:
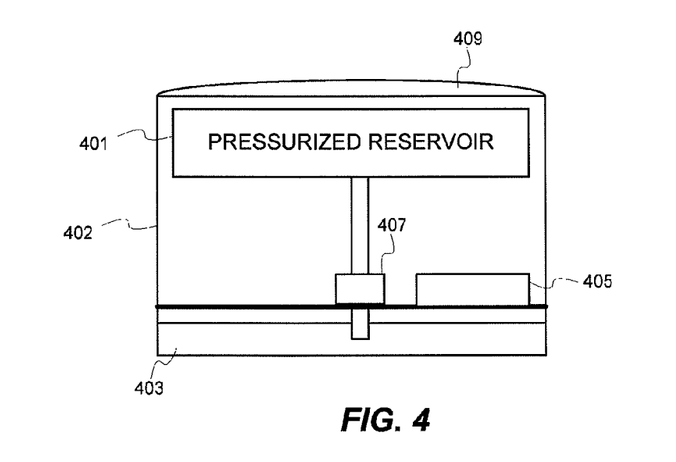
FIG. 4 is a schematic illustration of an alternative drug delivery device in accordance with the present invention

In an implementation shown in FIG. 4, a pressurized drug reservoir is used which minimizes or eliminates need for a micropump. Electronics control a valve that allows controlled quantities of the drug to be applied to the drug chamber where the formulation comes into contact with highly permeable membrane.

The construction and use of transdermal patches for the delivery of pharmaceutical agents is known. See, for example, U.S. Pat. No. 5,370,635 entitled "DEVICE FOR DELIVERING A MEDICAMENT" the disclosure of which is incorporated herein by reference. Such patches may be constructed using a saturated media, pressurized reservoirs, or unpressurized reservoirs with micropumps for continuous, pulsatile, or on-demand delivery of an active material. For example, a pharmaceutically acceptable composition of an active material may be combined with skin penetration enhancers including, but not limited to, oleic acid, amino acids, oleyl alcohol, long chain fatty acids, propylene glycol, polyethylene glycol, isopropanol, ethoxydiglycol, sodium xylene sulfonate, ethanol, N-methylpyrrolidone, laurocapram, alkanecarboxylic acids, dimethylsulfoxide, polar lipids, N-methyl-2-pyrrolidone, and the like, which increase the permeability of the skin to the active material and permit the active material to penetrate through the skin and into the bloodstream. Pharmaceutically acceptable compositions may be combined with one or more agents including, but not limited to, alcohols, moisturizers, humectants, oils, emulsifiers, thickeners, thinners, surface active agents, fragrances, preservatives, antioxidants, vitamins, or minerals. Pharmaceutically acceptable compositions may also be combined with a polymeric substance including, but not limited to, ethylcellulose, hydroxypropyl cellulose, ethylene/vinylacetate, polyvinyl pyrrolidone, and the like, to provide the composition in gel form, which may be dissolved in solvent such as methylene chloride, evaporated to the desired viscosity, and then applied to backing material to provide a patch. The backing can be any of the conventional materials such as polyethylene, ethyl-vinyl acetate copolymer, polyurethane and the like.

Figure 2A:
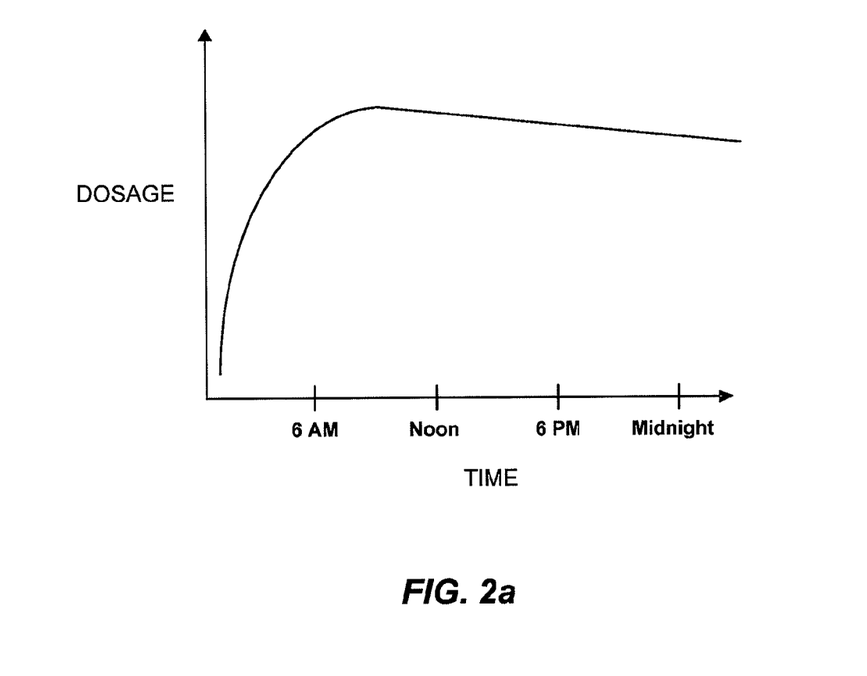
FIG. 2A and FIG. 2B illustrate comparative drug release profiles demonstrating operation of the present invention.
Figure 2B:
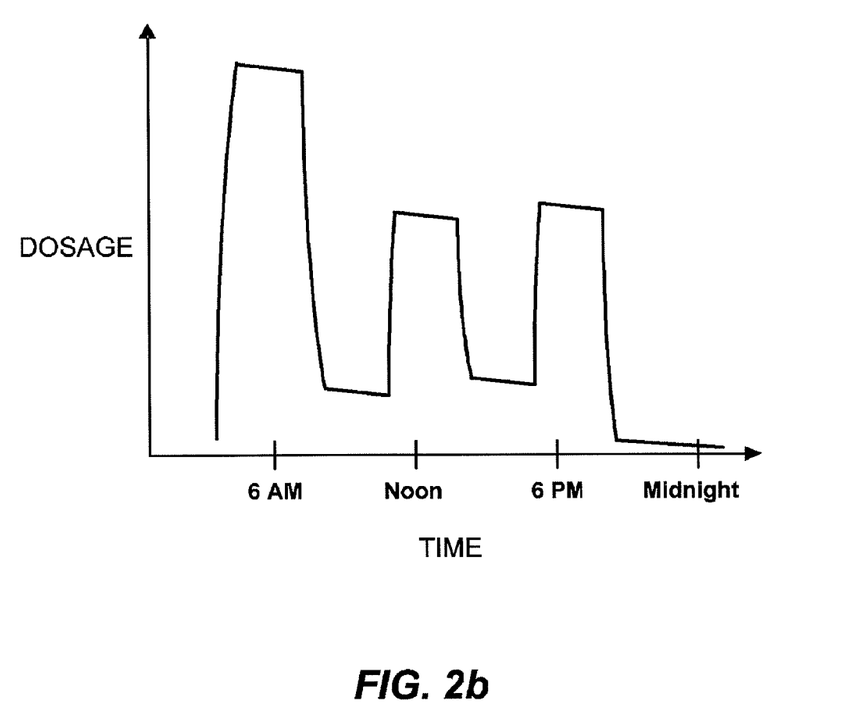

Example substances include caffeine and a variety of over-the-counter and prescription stimulants (for treating fatigue, sleep disorders, attention deficit disorders and a variety of other conditions), nicotine (for smoking cessation), nitroglycerin (for treating heart attack and strokes), fentanyl (for treating chronic pain), albutamol (for treating asthma), and selegiline (for treating depression, attention deficit disorder or Parkinson's disease). We have carefully identified these specific drugs and diseases because they have the following attributes: (i) Chrono-Pharmacology is critical to optimized dosing but is not being implemented because no automated transdermal system exists, and (ii) these drugs can be transdermally absorbed passively (i.e., without the need for ultrasound or electrical stimulation or other permeation enhancers). Exemplary chrono-pharmacological systems that can make use of the present invention are summarized in Table 1.

regiments for optimal therapy (FIG. 2B). There are many advantages for a controlled transdermal release of an active material such as a drug. As used herein, the term 'controlled' or 'sustained' release of an active material includes continuous or discontinuous, linear or non-linear release of the active material according to a programmed schedule. Among the advantages of controlled release are the convenience of a single application for the patient, avoidance of peaks and valleys in systemic concentration which can be associated with repeated injections, the potential to reduce the overall dosage of the active material, lower body stress, and the potential to enhance the pharmacological effects of the active material. A lower, sustained dose can also prevent adverse effects that are occasionally observed with infusion therapy. In addition to significantly reducing the cost of care, controlled release drug therapy can free the patient from repeated treatment or hospitalization, thus offering the patient greater flexibility and improving patient compliance. A controlled release formulation of certain drugs also provides an opportunity to use the drug in a manner not previously exploited or considered. The present invention is particularly advantageous when (i) known chrono-pharmacological information shows that a drug's effects can optimized when administered in a defined dosage at a predefined time or times, and/or (ii) patient compliance with the dosing

| DISEASES/CONDITION | CHRONOPHARMACOLOGY |
|---|---|
| Morning Lethargy | Adrenaline is lowest in the morning, making waking uncomfortable and difficult for many people. This can be treated by administering OTC Stimulant before waking |
| Smoking Cessation | Nicotine at night creates sleeping disorders (nightmares), but cravings are the highest after waking up. This can be treated by administering Nicotine before waking up. |
| Angina | Angina (variant) attacks occur 30 (thirty) times more often between 2:00 a.m. and 4:00 a.m. This can be treated by administering larger nitroglycerin doses in early morning |
| Asthma | Asthma attacks are 100 times more likely between 4:00 a.m. and 6:00 a.m. Adrenaline and Cortisol are virtually absent at night. This can be treated by administering albutamol in early morning |
| Colds and Flu | Heaviest symptoms overnight and in the morning. This can be treated by administering Cold/Flu medicine during the night. |
| Heart Attacks and Strokes | Heart attacks and strokes are most likely between 6:00 a.m. and Noon. This can be treated by administering Anticoagulants before waking up. |
| Pain | Neurological pain is worst between 3 A.M and 8 A.M. This can be treated by administering pain medication during sleep. |
| Depression | Selegiline at night can create sleeping disorders (nightmares), but depression symptoms are high immediately upon waking up. This can be treated by administering Selegiline before waking up. |
| Rheumatoid Arthritis | Worst upon awakening. Cortisol and anti-inflammatory hormones are very low at night. This can be treated by administering medication delivered before waking up. |
| Supplements | Vitamins and supplements are best administered in low doses over the course of the day to be most effective. |

Using this system the present invention can pre-program the times and amount of each dosage by precisely controlling the amount of drug exposed to the skin during each dosing. This feature is advantageous when a drug is best administered during sleep, e.g., 1 to 2 hours before waking up. The present invention precisely counteracts peak disease symptoms and increase patient compliance.

The present invention represents the first true non-invasive chrono-pharmacological drug delivery device. While current transdermal applications are restricted to the dosage profile shown in FIG. 2A, the automated implementation of the present invention can be programmed for a variety of drug delivery patterns to achieve customized patient dosing regimen is greatly increased due to automation, (doses required at inopportune times, when sleeping, for example).

A device according to the present invention in general comprises dispensing means, e.g. a pump, at least one drug reservoir, at least one administration element (patch reservoir, administration reservoir, administration compartment, administration chamber) and at least one solvent removal and/or recovery element and if necessary control means interconnected to each other. In a preferred embodiment of the invention the administration reservoir and the solvent recovery means are incorporated in an administration unit (patch). The at least one drug reservoir contains a sufficient amount of one or more active substance dissolved or dispersed at an appropriate concentration in a formulation which may contain a solvent or a solvent mixture that is volatile. If appropriate other excipients, for example tissue permeation promoters (enhancers), thickening substances, solubilizers, buffers, chemical stabilizers, preservatives are present too.

The active substance may be any dispensable fluid (for example a liquid, gel or powder), although liquids are particularly of use in the dispensing unit. In some embodiments, at least one of the reservoirs may contain an active substance in powder or other dry form. The powder or other agent is dispensed from the reservoir, and may be combined with a solvent and/or another liquid such as a penetration enhancer. If appropriate the dispensing unit may allow chemical reactions to occur, e.g. in the administration reservoir, as well as phase changes to stabilize (such as a change from a solid to a liquid state).

In operation the formulation contained in the at least one drug reservoir is dispensed by the dispensing unit into the at least one administration reservoir (patch reservoir). Volume and frequency of administration of the active substance are controlled by a control unit which preferably is freely programmable according to given needs. The solvent recovery means reclaim solvent that was dispensed together with the formulation into the patch reservoir and is not absorbed. The preferably volatile solvent evaporates from the interface continuously and is guided to the solvent recovery means. If appropriate a heating element or other helping means may be used for supporting evaporation of the solvent. However the temperature of the skin in general is sufficient. The solvent recovery means serve to remove depleted solvent from the interface such that, e.g. after repeated dispensing, active substance concentration maintains at a certain concentration and no unwanted substance is accumulated within the device. Upon quitting dispensing of formula, the residual solvent is recovered and dryness of the interface is achieved, which results in controlled termination of drug delivery. Alternatively or in addition depleted solvent may be discharged into environment only, e.g. by direct evaporation.

In general the active substance is completely enclosed in the administration/patch reservoir and is not in contact with the environment or other components. The interface may comprise a membrane (polymer membrane) which may be lined with an absorbent material, such as blotting paper, suitable to receive active substance and facing inwards to the interior of the device. The membrane of the interface is in functional contact with the surface to be treated. The drug formulation is dispensed onto the interface by the dispensing unit which is interconnected to the drug reservoir. The solvent recovery means are normally arranged at a certain distance from the absorbent material preventing uncontrolled absorption of solvent. The volume and frequency of dispensing are freely programmable and are used to control the delivery rate and the time pattern of delivery of the drug.

Drug is delivered from the interface primarily by diffusion. The solvent recovery element reclaims the solvent that was dispensed with the formulation onto the interface and was not absorbed otherwise. The solvent recovery element preferably is located within the device and comprises one or more desiccants and/or general adsorbents such as silica gel, molecular sieves or active carbon. These materials are normally arranged within a bag consisting of non-wettable but vapor permeable material e.g. such as GoreTex®. In a preferred embodiment the solvent recovery element is arranged close to but in non-contact with the interface. The volatile solvent evaporates from the interface continuously under the influence of body heat and the vapors are trapped in the solvent recovery element. The solvent recovery element serves the purpose of removing depleted solvent from the interface so that, after repeated dispensing, drug concentration maintains its highest value and no freely moving liquid is formed within the device. Upon quitting dispensing of drug formula, the residual solvent is recovered and dryness of the interface is achieved, which brings about stoppage of drug delivery. The solvent recovery element is contained in a non-wettable material in order to avoid uptake of drug formula and consequent loss of drug.

Several parameters are relevant for the amount of active substance absorbed by the surface to be treated such as concentration of the active substance in the solvent, the repetition-rate of supply and the volume supplied. These parameters are controllable by the described invention.

Solvent that is not absorbed by the skin in a sufficient way is carried off in another way than by absorption through the skin, e.g. by evaporation into the environment and/or by absorption by another means, e.g. absorbing substance such as silica gel. By this it is possible to avoid negative decrease of the concentration of active substance due to accumulation of the solvent which would impact the diffusion rate through the skin. Especially solvents based on water and/or alcohol are having at temperatures nearby the temperature of skin a vapor pressure which is sufficiently high to carry off the solvent by evaporation. However, the carrying off and/or diffusion rate of the solvent preferably is adjusted to the diffusion rate of the active substance through the skin to avoid accumulation of the solvent or precipitation of the active substance on the skin in a negative way.

The described invention offers the opportunity to precisely control the rate and the time pattern of systemic drug delivery. It can be applied to the delivery of drug into and/or across the skin. With the methodology according to the present invention the amount of active substance delivered per unit of time can be adjusted to values ranging between zero and a known maximum, the moments of time can be defined at which the delivery rate is set to a predetermined value and the delivery of drug over time spanning hours or days can be regulated in a programmed manner, e.g. using real time control. A device suitable to carry out the described technology offers the opportunity of fully automated transdermal drug delivery.

The method most widely used in prior art for automated controlled transdermal delivery is iontophoresis. With this method control of delivery of a drug is achieved by an electric current which is applied to the skin. By adjusting the current the delivery rate of the drug is regulated. Advantages of the present invention over iontophoresis are the ability to completely turn off delivery or reduce the delivery rate below a minimal value corresponding to passive skin permeation, the absence of skin irritation that the electric current may cause when applied to the skin and the low energy consumption compared to iontophoresis because normally no high currents are needed for extensive periods of time.

Conventional patch based delivery systems as known from prior art comprising a patch and a therewith interconnected dispensing unit are more or less suitable to administrate a chemical substance under a specific time regime, where the quantity of the specific dose delivered to the patch can be predetermined more or less accurate and each time period of dispensing the substance can be predetermined as well. However, turning delivery to a patch as known from prior art on and off causes uncontrolled time lag in the delivery rate to or through the skin. The delivery systems known from prior art often lead to a constantly diminishing dispensing rate. These problems are avoided by the present invention.

The disclosed invention offers a combination of formula dispensing with an on- and off-turning delivery of the formula and a simultaneous solvent recovery for the purpose of maintaining a constant and high drug delivery rate. The achievable delivery rate and the time lag due to on- and off-events result from the interplay between the rate of formula dispensing and the rate of solvent recovery. The former is preferably controlled by a freely programmable pump and the latter by amount and quality of the material of the solvent recovery element.

Precise control of delivery of the active substance is very important. Related thereto is the precise control of the solvent. The solvent may be controlled by additional means e.g. as described as follows.

A solvent removal system comprises a waste reservoir which is interconnected by a waste valve, e.g. a pinch valve, and/or a waste pump to the administration reservoir. In the case of a pin valve the waste valve preferably is driven by utilizing a wire made out of Shape-Memory-Alloy (SMA) or an alternative device pursuant to a preprogrammed regimen. In a given example the waste valve is opened or the waste pump is turned on such that the solvent is removed and e.g. brought in contact to a desiccant such that the solvent is safely absorbed. Proper administration may be achieved by opening and closing the connection to the waste reservoir by an appropriate time regime. In certain applications it is helpful to switch the connection to the waste reservoir with a certain delay with respect to the administration of the active substance. Instead or in addition to a pinch valve a micro pump may be appropriate to pump excessive solvent into a waste reservoir. In a further embodiment the tubing e.g. for depletion of solvent can comprise absorbent material which thereby is brought into direct contact with depleted carrier solution. It is possible to remove depleted fluid either pursuant to a preprogrammed profile or systematically, e.g. depleted fluid is brought into contact every 20 minutes with desiccant, by using a small lever or arm, or otherwise made to come into direct contact with the depleted carrier solution, resulting in absorption of the depleted carrier solution. Alternatively, a waste reservoir, e.g. a sponge, is lowered by a small lever or arm or otherwise to come into direct contact with the depleted carrier solution, resulting in immediate absorption of the depleted carrier solution. In a different embodiment a selectively permeable membrane surrounds a sponge or absorbent material, and the selectively permeable membrane primarily allows the solvent to pass through it (whether due to electric charge of the molecule or molecular size or acidity of the solvent vs. the drug or some other regulating means) and this semi permeable membrane either remains in constant contact with the diffusion surface or is periodically brought in to contact with the diffusion surface using an above described method. In a further embodiment a sponge or an absorbent material is in contact with the diffusion surface and a pre-tested and timed capillary action of the sponge is such that depleted carrier solution is absorbed at the right time and in proper amounts as to assist with the achievement of preprogrammed dosage profiles, i.e. even though much active substance may be absorbed along with the carrier solution still sufficient drug is present to achieve the objectives.

Modulated dispensing of drug formula brings about a significant increase of delivery rate over the one-time addition of formula at equal drug concentration. Thus, maximization of drug delivery rate is achieved. This is because the removal of solvent from the relatively small dispensed volume creates in situ an increase of drug concentration with subsequent saturation and precipitation of drug in the interface in immediate contact with the skin as evidenced by dryness of the interface. By the herein described method it is possible that the delivery rate of the active substance can be adjusted using the same drug solution by changing the dispensed volume of solution. Depending on the field of application it was found that about 2 gram of desiccant are sufficient for trapping solvent over at least 9 hours when e.g. dispensing 40 μl/hr of a given drug formula. It was found that increase of drug concentration in the formula causes a corresponding increase of delivery rate for dispensing of e.g. 40 μl/hr but not for e.g. 15 μl/hr. Apparently, dryness of the interface for the latter dispensing volume is achieved far before each consecutive dispensing step, thus hampering drug permeation.

Depending on the field of application, solvent removal means may be for example: a desiccant in a bag, any other absorbent material in a bag, a desiccant/absorbent connected to the interface by a tube, a desiccant/absorbent connected to the interface by a tube which comprises a valve, a compartment connected to the environment for evaporation, a compartment through which gas is guided to promote evaporation, an absorbent sponge, an absorbent sponge attached to an arm that moves it to and away from the interface, an absorbent sponge with a gas blowing device for drying. The material surrounding the solvent removal means preferably is made out of tissue, cloth, membrane, etc. The administration device (compartment) may comprise, if appropriate, at least one sensor, e.g. a humidity sensor for feedback control to the dispenser.

The solvent recovery means serves to remove depleted solvent from the active area of the administration reservoir such that the active substance concentration is maintained at a certain concentration and no unwanted substance is accumulated within the administration device. Upon quitting dispensing of formula into the administration device, the residual solvent is recovered and dryness of the interface is achieved, which results in controlled termination of drug delivery into skin. Normally the temperature of skin is sufficient to evaporate and discharge the solvent. However, a heating element or other helping means may be used for supporting evaporation.

The solvent recovery means are normally arranged at a certain distance from the interface, the administration reservoir respectively, is preventing uncontrolled absorption of solvent. The separation layer may e.g. comprise or consist of an inert foam or an appropriate cellular material or honeycomb. The solvent recovery means are preferably located within the administrative device and preferably comprise one or more desiccants and/or general or selective adsorbents such as silica gel, molecular sieves or active carbon preferably surrounded by a non-wettable material permeable for the vapors of solvent, e.g. such as Gore-Tex®.

Subsequent the method will be described in a general manner: The drug formulation is dispensed into the administration reservoir by the dispensing system. The volume and frequency of dispensing are freely programmable and are used to control the delivery rate and the time pattern of delivery of the chemical substance into the skin. The chemical substance is delivered from the administration reservoir by diffusion in the skin or onto the surface of the skin. The solvent recovery element reclaims solvent that was dispensed with the formulation into the administration reservoir. The solvent recovery element is in close vicinity to but in general not in direct contact with the administration reservoir to avoid uncontrolled absorption of solvent.

The volatile solvent evaporates from the interface under the influence of body heat and the vapors are trapped by the solvent recovery means, e.g. a chamber filled with absorbing material. The solvent recovery element serves the purpose of removing depleted solvent from the patch reservoir so that, after repeated dispensing, drug concentration maintains its highest value and no detrimental fluid (liquid) is accumulated within the administrating device. Upon quitting dispensing of drug formula, the residual solvent is recovered and dryness of the interface is achieved, which brings about stoppage of drug delivery.

Applications—ArisePatch™

A contemplated consumer product is the AntisePatch™. Most people experience difficulty and discomfort when waking early in the morning. According to a 2002 National Sleep Foundation poll 49% of US adults age 18-29 have trouble waking in the morning and 41% of US adults age 30-64 have trouble waking in the morning. There are 165,000,000 adults in the US alone age 18-64, meaning approximately 74,250,000 US adults age 18-64 have trouble waking in the morning.

Figure 5:
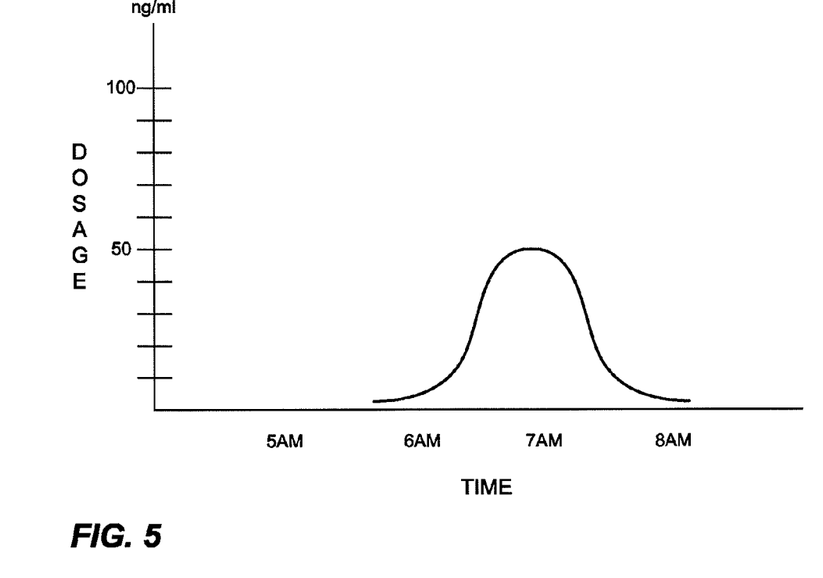
FIG. 5 shows an exemplary administration profile for a stimulant delivery system.

The AntisePatch implementation of the present invention allows individuals, while asleep, to have an over-the-counter (OTC) or prescription stimulant automatically administered during a 1-2 hour pre-wake-up period. FIG. 5 illustrates an exemplary stimulant administration profile showing a blood plasma level of ephedrine in nanograms per milliliter on the vertical axis, with time on the horizontal axis. Stimulant concentrations will reach peak levels immediately prior to having to wake. Immediately upon waking up the individual will be alert and feel well rested. The AntisePatch™ will eliminate the typical discomfort or difficulty associated with getting up early. This functionality is attractive to employed people getting up for work to ensure punctuality, and just about anyone who wants to offset morning discomfort associated with a late night, jet lag, or sickness.

Applications—Smoking Cessation

Nicotine replacement has been the most frequently used therapy to support smokers in their effort to quit. Smokers report that the craving for a cigarette is greatest immediately upon waking in the morning. The time elapsed between wakening and the first cigarette is the best indicator of addiction. For most smokers this time only a few minutes.

Current nicotine patches cause severe sleep disturbances by releasing nicotine steadily throughout the night to ensure sufficient morning nicotine levels to offset the strong morning craving. It is widely accepted that current nicotine patches have a detrimental and common side effect-sleeping disorders, and insomnia, including persistent nightmares. Therefore, users are often forced to remove the patch in the evening before they go to bed. This eliminates sleep disturbances, but results in nicotine levels that are insufficient to offset the strong morning craving. This is a major drawback to current nicotine patches and many users relapse, resulting in a less efficient smoking cessation therapy. Current patches present the user with a difficult decision, choosing between nightmares and relief from the strong morning cravings.

An exemplary product contemplated by the present invention is called Nicotine ChronoDose™ system. In accordance with the present invention, the system can begin to administer nicotine (or nicotine analogs or any other smoking cessation compound including but not limited to Zyban) automatically during a one hour period immediately prior to waking. This will relieve the smoker's peak craving upon waking without causing nightmares and insomnia. We believe that this system clearly provides a superior method for smoking cessation.

Figure 6:
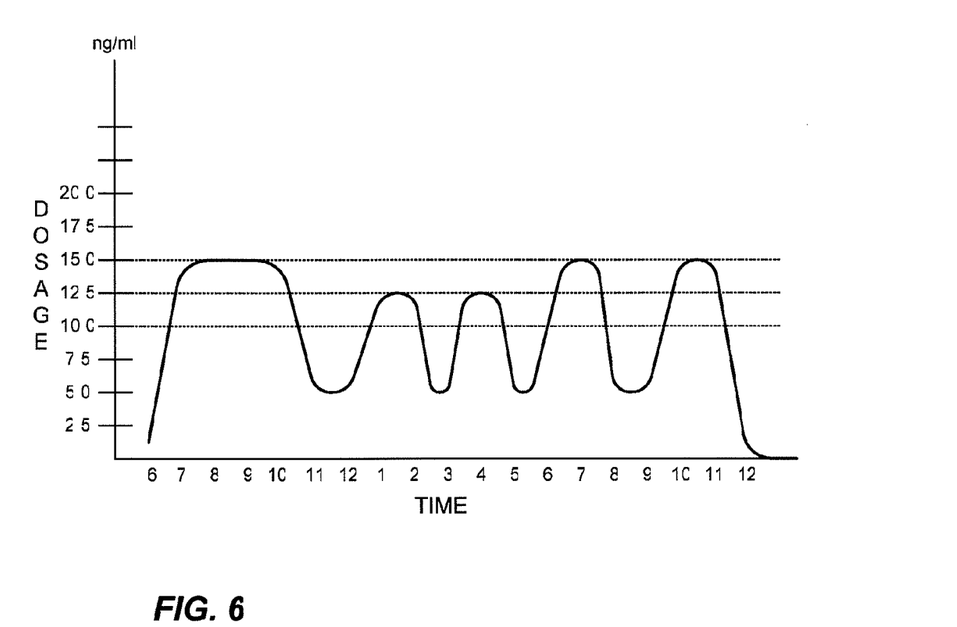
FIG. 6 shows an exemplary administration profile for a nicotine delivery system.

A more advanced nicotine replacement system than that described above is worn for three days at a time and is programmed to release nicotine in a daily rhythmic pattern such as shown in FIG. 6 to offset peaks in a smoker's cravings. FIG. 6 illustrates an exemplary nicotine administration profile showing a blood plasma level of nicotine in nanograms per milliliter on the vertical axis, with time on the horizontal axis. This implementation will reduce nicotine dependency by administering pre-programmed levels of nicotine pursuant to typical smoking patterns. For instance many smokers report that cravings for a cigarette are greatest upon waking up, after lunch, midafternoon, after dinner and before bedtime. This implementation of the present invention will automatically release larger doses of nicotine to offset peak cravings and no nicotine when cravings are typically at a minimum. The present invention may be delivered in a pre-programmed manner for each treatment regimen. The only involvement by the user will be the replacement of the 'reservoir' every three days, and the replacement of the platform housing as needed.

This implementation represents a tremendous move forward in nicotine replacement therapy, and is far superior to the old-technology systems that simply release the same amount of nicotine all day and night. With the present invention, one can systematically decrease a smoker's tolerance without increasing dependence (the result of a constant flow) and better wean a smoker off nicotine. This will allow the smoker to better 'tailor-down' and decrease the amount of nicotine he needs to quit. Modern smoking cessation is much more than nicotine replacement therapy. Programs also include weight control, diet and psychological support. The present invention fits well into these programs, since it addresses the key component of being able to quit smoking by efficiently countering the withdrawal symptoms while doing away with the negative side effects of current nicotine replacement therapy systems, namely sleep disturbance.

Applications—Cold and Flu Treatment

Cold and flu symptoms are worst from midnight until the early morning because the concentration of cortisol is lowest at that time. Current night time cold and flu medication end up losing efficacy by early morning when cold and flu symptoms are highest. Therefore people suffering from a cold or flu are often unpleasantly awoken by an increase in symptoms, cutting sleep short. Set and put on before bedtime, the present invention will automatically deliver a larger dose of medication and immuno-boosters in the early morning hours to more effectively combat the peak cold and flu symptoms that occur in the morning. Users will experience less severe cold and flu symptoms during the morning hours, will not have their sleep cycle cut short, and will wake up feeling symptom-free. This implementation uses prescription or OTC cold medicine alone or optionally in combination with certain transdermally efficacious vitamins and immune system boosters to provide a total solution to cold and flu ailments. This is the first cold therapy that combines OTC medicine with supplemental immuno-boosters in a comprehensive and automated manner. Our system will treat the cold symptoms directly and boost the body's immune system to help it heal naturally.

In a particular application, the Cold and Flu automated transdermal drug delivery system utilizes OTC cold medicine, Vitamin C, Echinacea, and Zinc to provide a total solution to cold and flu ailments, and all while you sleep.

Cold and flu symptoms are worst in the middle of the night and early morning because the hormone cortisol, a key inflammation fighter, is missing at that time. Cold and flu symptoms are worst from midnight until the early morning because the concentration of cortisol is lowest at that time. Current night time cold and flu medication end up losing efficacy by early morning when cold and flu symptoms are highest. Therefore people suffering from a cold or flu are often unpleasantly awoken by an increase in symptoms, cutting sleep short Set and put on before bedtime, the Cold and Flu automated transdermal drug delivery system utilizes our proprietary technology to automatically deliver a larger dose of medication and immuno-boosters in the early morning hours to more effectively combat the peak cold and flu symptoms that occur in the morning. Users will experience less severe cold and flu symptoms during the morning hours, will not have their sleep cycle cut short, and will wake up feeling symptom-free.

Our system not only combats statistically proven peak nighttime and early morning cold symptoms by releasing OTC cold medicine, but actually helps your body to heal by boosting its immune system through Vitamin C, Echinacea and Zinc supplementation in small but distinct doses all night long.

Our Cold/Flu system releases these combination of compounds every 2 hours throughout the night, with a higher dosage of compounds being released in the morning to combat these proven middle of the night and early morning symptoms, which are the worst of the day.

Cold and flu symptoms are worst in the middle of the night and early morning because the hormone cortisol, a key inflammation fighter, is missing at that time. Our system utilizes its core competitive advantage by pre-programming our System to release more medicaments precisely at that time to offset these peak symptoms. Current cold and flu medications end up losing efficacy by early morning when cold symptoms peak, so the user either has sleep cut short due to the onset of these symptoms, or wakes up out of slumber feeling sick with peak symptoms. Our system will ensure that a while a person is actually sleeping, a sufficient dose of cold and flu medicine is freshly delivered to offset these peak morning symptoms.

Applications—Weight Control, Vitamin and Herbal Supplementation

In yet another application, a series of weight loss vitamins and supplements is administered in small distinct doses many times over a multiple day period. Vitamins and supplements are absorbed by the body in small dosages. Contrary to popular belief, once-a-day products are not maximally effective because excess dosages are excreted unused. This implementation of the present invention precisely controls the timing and dosage of small but distinct amounts of vitamins and supplements during a 24 hour period to ensure that vitamins and supplements are constantly bio-available for optimal absorption and cellular function. Greater doses are automatically released prior to mealtimes to counter appetite cravings, resulting in a much more effective diet program.

Applications—Angina

Research shows that variant angina occurs 30 times more often between 2:00 a.m. and 4:00 a.m. ('critical angina phase') than at any other time of the day. Nitroglycerin effectively combats angina attacks, if administered in optimal doses. Current nitroglycerin patches exist, but they can only release a constant amount of nitroglycerine steadily over time. Current patches cannot tailor the release of nitroglycerine to optimize treatment by releasing more nitroglycerine precisely during the critical angina phase to offset these peak symptoms.

In addition, nitroglycerine loses its effectiveness and requires higher and higher dosages when administered constantly. Our bodies become tolerant to it. Current systems cannot stop or decrease the release of nitroglycerine when disease symptoms are lowest. Thus, these current 'dumb' patches cannot offset the critical angina phase by releasing more of the drug, nor can they shut down or stop nitroglycerine administration when the body doesn't need it. It is a 'one dose fits all' type of scenario once each "dumb" patch is applied to the patient.

The method in accordance with the present invention utilizes an automated transdermal system in order to transdermally administer more nitroglycerine during the critical angina phase to ensure adequate offset of these symptoms and less nitroglycerine when it is not needed so that no tolerance builds up. Our method utilizes a 'smart' patch medicine system at this time to offset these peak critical phases in the disease cycle arising due to the human body's circadian rhythm.

The preprogrammable automated transdermal system is worn around the wrist like a watch (or the forearm arm or ankle) and releases nitroglycerine in optimal dosages at times that are optimally synchronized. This is pursuant to a pre-programmed and tailored dosage profile. Current nitroglycerin patches only have the capability to release a constant dose of nitroglycerin over a period of time. Current nitroglycerin patches simply cannot alter or vary dosages to increase dosages at different times of the day, and decrease dosages at other times of the day.

The nitroglycerin system in accordance with the present invention has three primary advantages over current nitroglycerin patches. First, the system utilizes its core competitive advantage to automatically and precisely release nitroglycerin in peak amounts to offset the peak symptoms of morning attacks occurring during the critical angina phase. Current nitroglycerine patches have release rates that stay constant and do not increase to offset critical phases, and do not decrease as symptoms decrease. Second, our system solves the tolerance issue by releasing less (or no) nitroglycerin in off-peak hours, and then releasing nitroglycerin at just the right time so that it is present during critical periods, without increasing tolerance. Third, our system accomplishes 1 and 2 above automatically, without the need for a patient to wake up to take a drug at this critical phase, which does away with the need for any increased patient compliance.

As a result we believe that our nitroglycerin system represents an ideal delivery system for patients who use nitroglycerin regularly for the treatment and/or the prevention of heart attacks and strokes. Patient compliance regarding the timing and dose of heart attack medication is crucial. Patient non-compliance with physician's instructions for this is often a cause of re-hospitalization, according to the US Department of Health and Human Services. The system solves this problem, and will decrease the need for re-hospitalization by dramatically increasing patient compliance.

This system can be either an 'wear each night and remove in the morning' system, whereby it only releases nitroglycerine automatically to offset the critical angina phase in the morning, or a 'total solution' system, that is worn for a period of 24 hours to several days, and that administers nitroglycerine in tailored amounts and at tailored times as synchronized with the body's circadian rhythm (and conveniently taken off while showering or swimming).

The system is an innovative new drug therapy for angina. With its superior advantage of optimized and automated time and dose administration synchronized with our circadian rhythms, the system in accordance with the present invention ensures that nitroglycerin will circulate in the bloodstream exactly when the patient needs it, and without any build up tolerance. For these reasons, our system is superior to current steady release nicotine patches. Our system's increased advantages are extremely relevant for those patients with moderate to severe angina.

Figure 7:
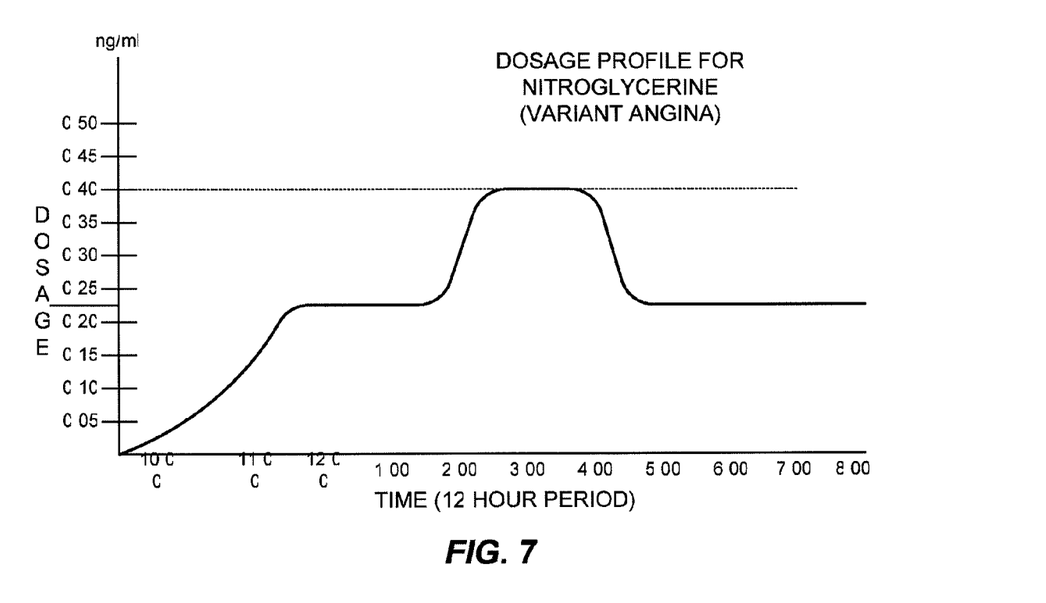
FIG. 7 shows an exemplary administration profile for a nitroglycerine delivery system tailored to treat variant angina attacks.

FIG. 7 shows an exemplary administration profile for a nitroglycerine delivery system tailored to treat variant angina attacks or angina pectoris. This type of angina attack has a peak frequency in many patients between the hours of 2:00 and 4:00 AM. This is a particularly difficult time to wake up to take a drug such as nitroglycerine. In accordance with the present invention an administration profile substantially like that shown in FIG. 7 is automatically administered. In FIG. 7 the vertical axis indicates blood plasma level in nanograms per milliliter, and the horizontal axis indicates time from 10:00 PM through the night to 8:00 AM.

Figure 8:
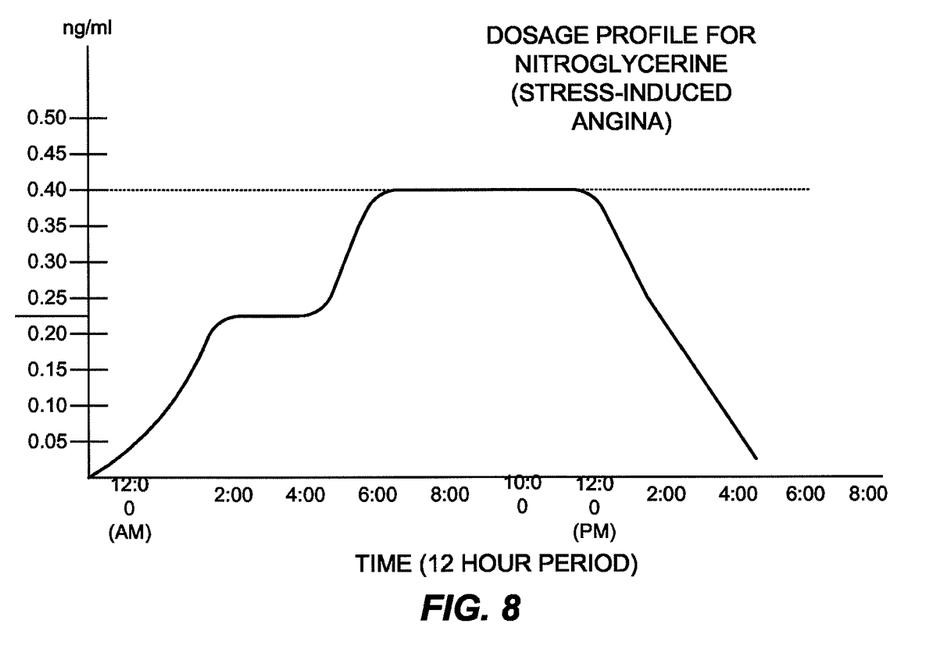
FIG. 8 illustrates an exemplary administration profile for a nitroglycerine delivery system tailored to treat stress-induced angina attack.

FIG. 8 illustrates an exemplary administration profile for a nitroglycerine delivery system tailored to treat stress-induced angina attack. In FIG. 8 the vertical axis indicates blood plasma level in nanograms per milliliter, and the horizontal axis indicates time from 12:00 AM through the day until about 4:00 PM. The administration profile shown in FIG. 8 provides a high blood plasma concentration throughout the waking hours of a day when stress is likely occur.

Applications—Asthma

The automated transdermal asthma system automatically administers a morning dose of albuterol, tolobuterol, salmeterol, beta 2 agonist or any other antiarrhythmic drug (an 'Asthma drug') to combat the peak symptom of morning asthma attacks known as the 'morning dip'.

Asthma attacks occur 100 (one hundred) times more often between the hours 4 A.M. and 6 A.M., when most people are asleep. This is due to the early morning deterioration of respiratory function known as 'morning dip', which is the time of day that respiratory function is at its lowest. These early morning asthma attacks cause great distress to sufferers and care providers. The morning dip represents the dip in respiratory function at this time when asthma attacks are 100 times more likely to occur. Our system effectively combats the morning dip by releasing more Asthma drug at this time to offset this peak morning symptom. In other words, our 'smart' patch varies the level of drug in the bloodstream so that drug concentrations are highest when respiratory function is at its lowest.

Current 'dumb' asthma patches exist, but they can only release a constant amount of drug steadily over time. Current patches cannot tailor the release of drug to optimize treatment by releasing more drug precisely during the morning dip to offset these peak critical symptoms.

The Asthma system has two primary advantages over current patches. First, the system of the present invention utilizes its core competitive advantage to automatically and precisely release albuterol or other asthma drugs in peak amounts to offset the peak symptoms associated with the morning dip. Current patches have release rates that stay constant and do not increase to offset this peak critical phases, and do not decrease as symptoms decrease. Second, our system accomplishes 1 and 2 above automatically, without the need for a patient to wake up to take a drug at this critical phase, which does away with the need for any increased patient compliance.

The automated transdermal system for Asthma is worn around the wrist like a watch (or the forearm arm or ankle) and releases albuterol or other Asthma drugs in optimal dosages at times that are optimally synchronized, especially to offset the morning dip, pursuant to a pre-programmed and tailored dosage profile. Current Asthma patches only have the capability to release a constant dose over a period of time. Current Asthma patches simply cannot alter or vary dosages to increase dosages at different times of the day, and decrease dosages at other times of the day.

The system is an innovative new drug therapy for asthma. With its superior advantage of optimized and automated time and dose administration synchronized with our circadian rhythms, our system ensures that albuterol or another asthma drug will circulate in increased amounts in the bloodstream exactly when the patient needs it. For these reasons, our system is superior to current steady release patches. Our system's increased advantages are extremely relevant for those patients with moderate to severe asthma.

Applications—Hypertension

The clondine automated transdermal system utilizes clondine, (or another hypertension drug) an effective drug that combats high blood pressure. The clondine automated transdermal drug delivery system has an automated morning release of clondine to combat the peak symptom of morning heart attacks.

Blood pressure differs at different times of the day. Blood pressure surges upon waking, and is lower by 20 to 30 percent while sleeping. Our preprogrammed automatic transdermal system utilizes its core competitive advantage by releasing clondine in a tailored fashion to counter high blood pressure when symptoms are highest, while releasing less clondine when symptoms are less severe.

Current clondine patches release the drug consistently over time. It cannot release more of the drug when symptoms are worst. People die most when the symptoms peak. Having the advantage of administering more of the drug when a patient needs it the most can mean the difference between life and death, especially in patients with moderate to severe high blood pressure.

The automated transdermal system for hypertension has two primary advantages over current patches. First, our system utilizes its core competitive advantage to automatically and precisely release clondine or other hypertension drugs in peak amounts to offset the peak symptoms associated with the dangerous morning symptoms. Current hypertension patches have release rates that stay constant and do not increase to offset this peak critical phases, and do not decrease as symptoms decrease. Second, our system accomplishes 1 and 2 above automatically, without the need for a patient to wake up to take a drug at this critical phase, which does away with the need for any increased patient compliance.

Applications—Depression, Alzheimer's, Attention Deficit

The selegiline automated transdermal system utilizes selegiline, an effective MAO inhibitor for the treatment of depression, Alzheimer's and Attention Deficit Disorder.

The selegiline automated transdermal drug delivery system gives an automated morning release of selegiline to combat the peak symptom of morning depression without the side effect of sleep disturbances.

The system in accordance with the present invention is applied before bed. It does not release the drug until an hour or 2 before morning, so symptom of morning depression would be corrected by our system without subjecting the patient to sleep disturbances.

Primary negative side effects of the selegiline patches are abnormal dreams, insomnia, and difficulty sleeping. We believe that by specifically refraining from administering selegiline at night, and utilizing our system's core competitive advantage to turn it on an hour or so before waking, we can do away with this negative side effect and still offset the critical phase of morning symptoms of depression. It has been reported that patients have increased symptoms of depression upon waking if the critical amount of Selegiline is not circulating through their system. Our system utilizes its core competitive advantage to provide a compelling solution to this problem. Our system is applied before bed, it would not release the drug until an hour or two before morning, so symptom of morning depression would be corrected by our system without subjecting the patient to sleep disturbances Current Oral Selegiline produces horrible side effects. There is a new Selegiline patch coming out on the market, but it to produces sleep disturbances. It is believed that the system in accordance with the present invention would be superior to conventional Selegiline product delivery systems.

Applications—In General

The present invention is particularly useful in applications in which it is necessary and/or desirable to start the administration of a drug, stop the administration of a drug, and/or increase/decrease the dosage of a drug at a time when it is inconvenient or impossible for a patient to initiate the necessary actions. This is particularly useful for a wide variety of drug administration applications that benefit when administration is started, stopped, or changed while a person is sleeping. As chronotherapy knowledge increases, it is contemplated that a wide variety of applications will be discovered in which benefit is realized by starting, stopping and/or changing the drug administration while a patient sleeps.

In each of the examples, treatment is continued as needed to provide superior symptomatic relief, prevent exacerbation of symptoms, and/or prevent and/or delay progression of the disease state or condition in the patient, or until it is no longer well tolerated by the patient, or until a physician terminates treatment. For example, a physician may monitor one or more symptoms and/or serum levels of active material and/or metabolic by-product(s) in a patient being treated according to this invention and, upon observing attenuation of one or more symptoms for a period of time, conclude that the patient can sustain the positive effects of the above-described treatment without further administration for a period of time. When necessary, the patient may then return at a later point in time for additional treatment as needed.

As used herein, 'day' means a 24-hour period. Thus, for example, 'for at least three consecutive days' means for at least a 72-hour period. During or after the treatment, a physician may monitor one or more symptoms and/or serum levels in the patient and, upon observing an improvement in one or more of the parameters for a period of time, conclude that the patient can sustain the positive effects of the treatment without further administration of the active material for a period of time.

In order to use an active material for therapeutic treatment (including prophylactic treatment) of mammals including humans according to the methods of this invention, the active material is normally formulated in accordance with standard pharmaceutical practice as a pharmaceutical composition. According to this aspect of the invention there is provided a pharmaceutical composition comprising an active material in association with a pharmaceutically acceptable diluting substance or carrier, wherein the active material is present in an amount for effective treating or preventing a particular condition. While individual needs may vary, determination of optimal ranges for effective amounts of an active ingredient (alone or in combination with other drugs) within the ranges disclosed herein is within the expertise of those skilled in the art. Accordingly, 'effective amounts' of each component for purposes herein are determined by such considerations and are amounts that improve one or more active ingredient functions and/or ameliorate on or more deleterious conditions in patients and/or improve the quality of life in patients.

The present invention also provides pharmaceutical kits for treating a particular symptom, condition and/or disease and/or improving a particular biological function, comprising one or more containers comprising one or more active compositions in accordance with this invention. Such kits can also include additional drugs or therapeutics for co-use with the active composition for treatment or prevention of a particular symptom, condition and/or disease and/or improving a particular biological function. In this embodiment, the active composition and the drug can be formulated in admixture in one container, or can be contained in separate containers for simultaneous or separate administration. The kit can further comprise a device(s) for administering the compounds and/or compositions, such as device 100 shown in FIG. 1, and written instructions in a form prescribed by a governmental agency regulating the manufacture, use or sale of pharmaceuticals or biological products, which instructions can also reflect approval by the agency of manufacture, use or sale for human administration.

Although the invention has been described and illustrated with a certain degree of particularity, it is understood that the present disclosure has been made only by way of example, and that numerous changes in the dosages, administration profiles, timing, as well as the combination and arrangement of parts can be resorted to by those skilled in the art without departing from the spirit and scope of the invention, as hereinafter claimed.

What is claimed is:

1. A method for delivering an active substance to a user, the method comprising:
    placing a delivery device in contact with the user's skin, the dispensing device comprising a reservoir, a skin interface, a programmable dosage controller configured to control the time and dosage of the active substance according to a dosage profile corresponding to a circadian rhythm of the user, and a solvent recovery element;
    dispensing a first portion of the active substance and solvent from the reservoir to the skin interlace according to the dosage profile;
    delivering the active substance through the skin interface to the skin; and
    removing a portion of the solvent from the skin interface and trapping the solvent within the solvent recovery element to control active substance delivery according to the dosage profile.

2. The method of claim 1, wherein the skin interlace comprises a highly permeable membrane.

3. The method of claim 2, further comprising diffusing the active substance across a surface, area of the highly permeable membrane.

4. The method of claim 3, wherein delivering the active substance through the skin interface includes delivering the active substance across a surface area of the highly permeable membrane to the skin.

5. The method of claim 1, wherein the programmable dosage controller is configured to control a valve in fluid communication with the reservoir.

6. The method of claim 1, wherein the delivery device is adhesively attached to the skin.

7. The method of claim 1, wherein the programmable dosage controller comprises timing routines corresponding to the circadian rhythm.

8. The method of claim 7, wherein the timing routines are selected to deliver the active substance at a time, rate, sequence and/or cycle corresponding to the circadian rhythm.

9. The method of claim 1, wherein the active substance comprises nicotine and the dosage profile is configured to deliver the nicotine at times that are associated with nicotine cravings.

10. The method of claim 9, wherein at least one of the times corresponds to a time at which the user experiences a morning nicotine craving.

11. The method of claim 1, Further comprising: removing the delivery device after contacting the skin for greater than 24 hours.

12. The method of claim 1, further comprising: removing the delivery device after contacting the skin for greater than 72 hours.

13. The method of claim 1, wherein the reservoir contains the active substance and solvent.

14. The method of claim 13, further comprising: replacing the reservoir with a second reservoir containing an active substance and a solvent.

15. The method of claim 14, further comprising: using the delivery device with the second reservoir for greater than 72 hours.

16. The method of claim 1, wherein the solvent recovery element is a waste reservoir.

17. The method of claim 1, wherein the active substance comprises a stimulant and the dosage profile is configured to deliver the stimulant during a 1-2 hour pre-wake-up period.

18. The method of claim 1, wherein the active substance comprises cold medicine and the dosage profile is configured to deliver the cold medicine while the user sleeps.

19. The method of claim 18, further comprising dispensing vitamins and/or minerals to the skin interface while the user sleeps.

20. The method of claim 1, wherein the active substance comprises nitroglycerine and the dosage profile is configured to deliver the nitroglycerine while the user sleeps in first amount in a first time period and in a second amount higher than the first amount in a second time period.

21. The method of claim 1, wherein the active substance is an asthma drug and the dosage profile is configured to deliver the asthma drug while the user sleeps.

22. The method of claim 1, wherein the active substance is a hypertension drug and the dosage profile is configured to deliver the hypertension drug while the user sleeps.

23. The method of claim 1, wherein the active substance is selegiline and the dosage profile is configured to deliver the selegiline while the user sleeps.

24. A method for delivering an active substance to a user, the method comprising:
  placing a delivery device in contact with the user's skin, the dispensing device comprising a reservoir, a skin interface, a programmable dosage controller configured to control the time and dosage of the active substance according to a dosage profile and a solvent recovery element;
  dispensing a first portion of the active substance and solvent from the reservoir to the skin interface according to the dosage profile;
  removing a portion of the solvent from the skin interface into the solvent recovery element to control active substance concentration and to control active substance delivery according to the dosage profile; and
  delivering the active substance through the skin interface to the skin in discreet doses over a 24 hour period to ensure consistent bioavailability.

25. A method for delivering an active substance and to a user, the method comprising:
  placing a delivery device in contact with the user's skin, the dispensing device comprising a reservoir, a skin interface, a programmable dosage controller configured to control the time and dosage of the active substance according to a dosage profile and a solvent recovery element;
  dispensing a first portion of the active substance and solvent from the reservoir to the skin interface according to the dosage profile;
  removing a portion of the solvent from the skin interface into the solvent recovery element to control active substance concentration and to control active substance delivery according to the dosage profile; and
  delivering the active substance through the skin interface to the skin in greater amounts upon wake up and at meal times to assist with weight loss.

* * * * *